United States Patent
Tamamushi

(10) Patent No.: US 8,306,310 B2
(45) Date of Patent: Nov. 6, 2012

(54) APPARATUS AND METHOD FOR PATTERN INSPECTION

(75) Inventor: Shuichi Tamamushi, Kanagawa (JP)

(73) Assignee: NuFlare Technology, Inc., Numazu-shi (JP)

( * ) Notice: Subject to any disclaimer, the term of this patent is extended or adjusted under 35 U.S.C. 154(b) by 581 days.

(21) Appl. No.: 12/551,908

(22) Filed: Sep. 1, 2009

(65) Prior Publication Data

US 2010/0067778 A1     Mar. 18, 2010

(30) Foreign Application Priority Data

Sep. 16, 2008 (JP) ................................. 2008-236964
Mar. 19, 2009 (JP) ................................. 2009-067661

(51) Int. Cl.
*G06K 9/00* (2006.01)
*G01N 21/00* (2006.01)

(52) U.S. Cl. ..................... 382/145; 382/154; 356/237.4; 356/237.5

(58) Field of Classification Search .................. 382/145, 382/141, 149, 151, 154; 356/237.1–237.5
See application file for complete search history.

(56) References Cited

U.S. PATENT DOCUMENTS

| | | | | |
|---|---|---|---|---|
| 4,849,914 A | * | 7/1989 | Medioni et al. | 382/112 |
| 6,169,603 B1 | * | 1/2001 | Takayama | 356/500 |
| 6,744,511 B1 | * | 6/2004 | Saiki et al. | 356/399 |
| 7,065,240 B2 | * | 6/2006 | Tada | 382/145 |
| 7,487,491 B2 | * | 2/2009 | Oaki et al. | 716/51 |
| 7,911,599 B2 | * | 3/2011 | Watanabe et al. | 356/237.5 |
| 8,019,144 B2 | * | 9/2011 | Sugihara | 382/141 |
| 2007/0047799 A1 | * | 3/2007 | Isomura | 382/147 |
| 2008/0234939 A1 | * | 9/2008 | Foot et al. | 702/12 |

FOREIGN PATENT DOCUMENTS

JP   2008-112178   5/2008

* cited by examiner

*Primary Examiner* — Sang Nguyen
(74) *Attorney, Agent, or Firm* — Oblon, Spivak, McClelland, Maier & Neustadt, L.L.P.

(57) ABSTRACT

A pattern inspection apparatus includes a light source, a stage configured to mount thereon a substrate with a pattern formed thereon, a first laser measuring unit configured to measure a position of the stage by using a laser beam, a sensor configured to capture a pattern image obtained from the pattern, formed on the substrate, irradiated by light from the light source, an optical system configured to focus the pattern image on the sensor, a second laser measuring unit configured to measure a position of the optical system by using a laser beam, a correction unit configured to correct a captured pattern image by using a difference between the position of the stage and the position of the optical system, and an inspection unit configured to inspect whether there is a defect of the pattern by using a corrected pattern image.

10 Claims, 13 Drawing Sheets

APPARATUS AND METHOD FOR PATTERN INSPECTION

CROSS-REFERENCE TO RELATED APPLICATION

This application is based upon and claims the benefit of priority from the prior Japanese Patent Application No. 2008-236964 filed on Sep. 16, 2008 in Japan, and the prior Japanese Patent Application No. 2009-067661 filed on Mar. 19, 2009 in Japan, the entire contents of which are incorporated herein by reference.

BACKGROUND OF THE INVENTION

1. Field of the Invention

The present invention relates to a pattern inspection apparatus and a pattern inspection method, and more particularly to an apparatus and method with a function of correcting a distortion of a captured image.

2. Description of Related Art

The lithography technology which promotes micro-miniaturization of semiconductor devices is extremely important as being the only process whereby patterns are formed, in the semiconductor manufacturing. In recent years, with the high integration of LSI, the line width (critical dimension) required for semiconductor device circuits is decreasing year by year. Then, in order to form a desired circuit pattern on such semiconductor devices, there is a need for a highly accurate master or "original" pattern (also called a mask or a reticle).

Since the LSI manufacturing requires a tremendous amount of manufacturing cost, it is crucial to improve its yield. One of major factors that decrease the yield of the LSI manufacturing is a pattern defect of a mask used when exposing (transferring) a fine pattern onto a semiconductor wafer by the photolithography technology. In recent years, with miniaturization of an LSI pattern formed on a semiconductor wafer, dimensions of defects to be detected have become extremely small. Thus, a pattern inspection apparatus for inspecting defects of a mask for exposure used in manufacturing LSI needs to be highly accurate.

As an inspection method, it is known that an optical image of a pattern formed on a target object or "sample", such as a lithography mask, imaged at a predetermined magnification using a magnifying optical system is compared with design data or an optical image of an identical pattern on the target object. For example, the following is known as pattern inspection methods: "die to die inspection" method that compares data of optical images of identical patterns at different positions on the same mask, and "die to database inspection" method that inputs into the inspection apparatus the writing data (design pattern data) converted from pattern-designed CAD data to a format for input to the writing apparatus when writing a pattern on a mask, generates design image data (reference image) based on the input writing data, and compares the generated design image data with an optical image (measurement data) obtained by capturing an image of the pattern. According to the inspection method of the inspection apparatus, a target object is positioned on a stage so that a light flux may scan the object by the movement of the stage. Specifically, the target object is irradiated with a light flux from the light source and the illumination optical system. Light transmitted through the target object or reflected therefrom is focused on a sensor through the optical system. An image captured by the sensor is transmitted as measurement data to a comparison circuit. In the comparison circuit, after position alignment of the images, measurement data and reference data are compared in accordance with an appropriate algorithm. If there is no matching between the data, it is judged that a pattern defect exists (refer to, e.g., Japanese Patent Application Laid-open (JP-A) No. 2008-112178).

As a technique for exposing a fine pattern exceeding a wavelength limit, there are a double exposure technique and a double patterning technique, for example. In these techniques, since two masks are used, there is a case that a local positional deviation of a pattern, which is not usually recognized as a defect in the inspection of each mask, may be a defect when superimposing patterns of both the masks. Therefore, the local positional deviation of the pattern could give a large influence on the yield. Thus, in the inspection apparatus, it is necessary to locally detect a distortion at an absolute position. However, if an image captured by the inspection apparatus is distorted, it becomes difficult to highly accurately detect the distortion at the absolute position. As one of the causes of an image distortion, it can be cited that a relative position between the optical system, from the stage to the sensor, and the stage may deviate due to a thermal expansion, deformation, etc. of the pedestal, etc. of the inspection apparatus. There has been no sufficient solution that suppresses the image distortion caused by the positional deviation of the optical system.

As mentioned above, as one of the causes of an image distortion, it can be cited that a relative position between the optical system, from the stage to the sensor, and the stage may deviate due to a thermal expansion, deformation, etc. of the pedestal, etc. of the inspection apparatus. There has been no sufficient solution that suppresses the image distortion caused by the positional deviation of the optical system.

BRIEF SUMMARY OF THE INVENTION

It is an object of the present invention to provide an inspection apparatus and method capable of correcting an image distortion caused by a positional deviation of the optical system.

In accordance with one aspect of the present invention, a pattern inspection apparatus includes a light source, a stage configured to mount thereon a substrate with a pattern formed thereon, a first laser measuring unit configured to measure a position of the stage by using a laser beam, a sensor configured to capture a pattern image obtained from the pattern, formed on the substrate, irradiated by light from the light source, an optical system configured to focus the pattern image on the sensor, a second laser measuring unit configured to measure a position of the optical system by using a laser beam, a correction unit configured to correct a captured pattern image by using a difference between the position of the stage and the position of the optical system, and an inspection unit configured to inspect whether there is a defect of the pattern by using a corrected pattern image.

In accordance with another aspect of the present invention, a pattern inspection method includes measuring a position of a stage configured to mount thereon a substrate with a pattern formed thereon, by using a laser beam, capturing a pattern image obtained from the pattern, formed on the substrate, irradiated by light from a light source, by using a sensor, measuring a position of an optical system which focuses the pattern image on the sensor, by using a laser beam, correcting a captured pattern image by using a difference between the position of the stage and the position of the optical system, and inspecting whether there is a defect of the pattern by using a corrected pattern image.

DETAILED DESCRIPTION OF THE INVENTION

Embodiment 1

Figure 1:
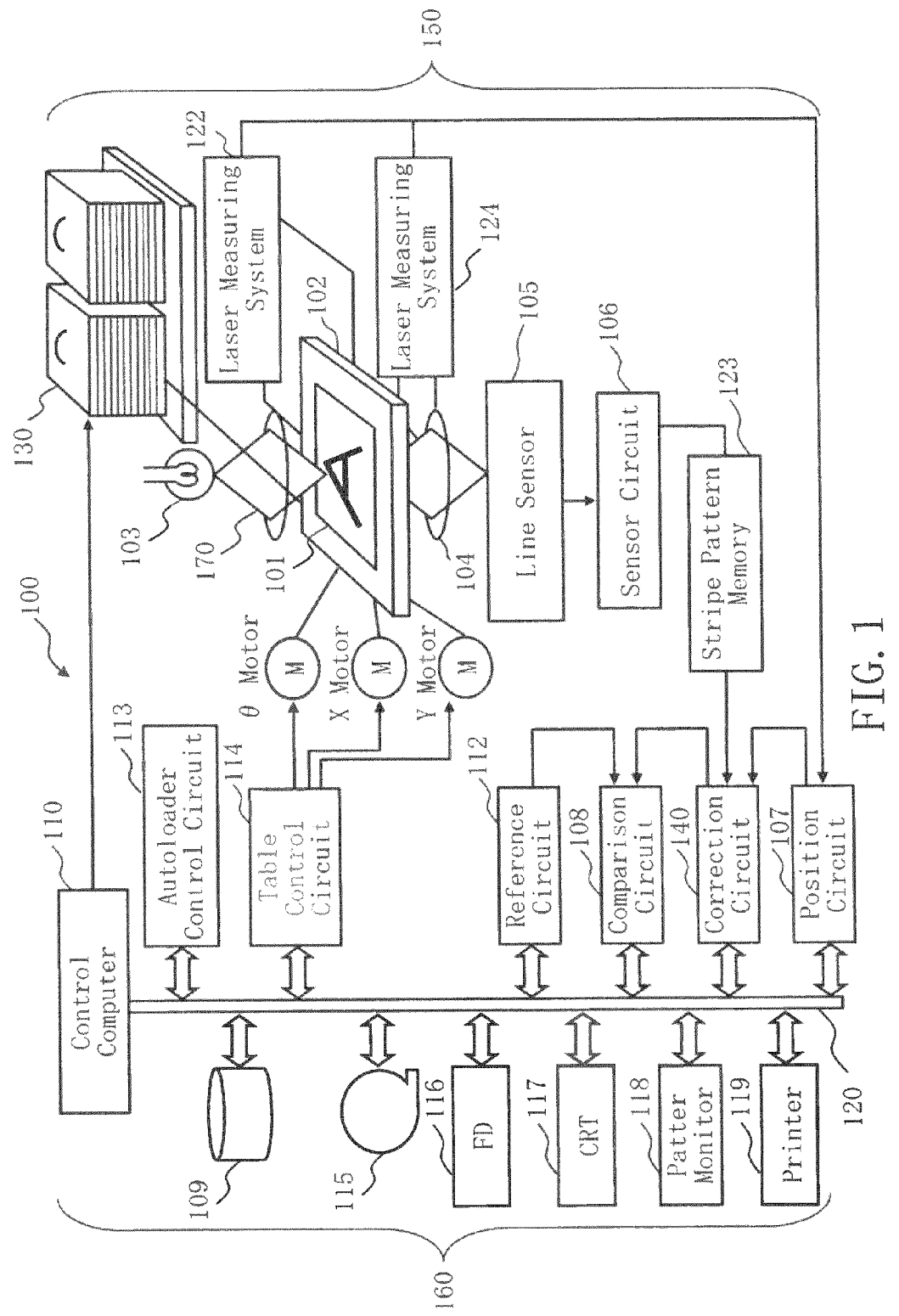
FIG. 1 is a schematic diagram showing a structure of a pattern inspection apparatus according to Embodiment 1.

FIG. 1 is a schematic diagram showing a structure of a pattern inspection apparatus according to Embodiment 1. In FIG. 1, an inspection apparatus 100 for inspecting defects of a target object, such as a mask, includes an optical image acquisition unit 150 and a control system circuit 160. The optical image acquisition unit 150 includes a light source 103, an XYθ table 102, an illumination optical system 170, a magnifying optical system 104, a line sensor 105, a sensor circuit 106, a laser measuring system 122, and an autoloader 130. In the control system circuit 160, a control computer 110 is connected, through a bus 120, to a position circuit 107, a correction circuit 140, a comparison circuit 108, a reference circuit 112, an autoloader control circuit 113, a table control circuit 114, a magnetic disk drive 109, a magnetic tape drive 115, a flexible disk drive (FD) 116, a cathode ray tube (CRT) 117, a pattern monitor 118, and a printer 119. Moreover, the sensor circuit 106 is connected to a stripe pattern memory 123 which is connected to the correction circuit 140. The XYθ table 102, which is an example of the stage, is driven by an X-axis motor, a Y-axis motor, and a θ-axis motor. FIG. 1 depicts structure elements necessary for describing Embodiment 1, and it should be understood that other structure elements generally necessary for the inspection apparatus 100 may be included therein.

In the inspection apparatus 100, an inspection optical system of large magnification is composed of the light source 103, the XYθ table 102, the illumination optical system 170, the magnifying optical system 104, the line sensor 105, and the sensor circuit 106. The XYθ table 102 is driven by the table control circuit 114 under the control of the control computer 110. The XYθ table 102 can be moved by a drive system such as a three-axis (X-Y-θ) motor, which drives the XYθ table 102 in the X direction, the Y direction, and the θ direction. For example, a step motor can be used as each of these X, Y, and θ motors. The moving position of the XYθ table 102 is measured by the laser measuring system 122 and supplied to the position circuit 107. Moreover, the moving position of the magnifying optical system 104 is measured by the laser measuring system 124, and supplied to the position circuit 107. A photomask 101 on the XYθ table 102 is automatically conveyed from the autoloader 130 driven by the autoloader control circuit 113, and automatically ejected after the inspection.

The photomask 101, being an inspection target object to be inspected, is placed on the XYθ table 102 movable in a horizontal direction and a rotating direction by the X-, Y-, and θ-axis motors. The photomask 101 has a pattern formed thereon. Then, the pattern formed on the photomask 101 is irradiated by continuous light emitted from a suitable light source 103, thorough the illumination optical system 170. The light having penetrated the photomask 101 is focused, through the magnifying optical system 104, on the line sensor 105 as an optical image and enters in it. As the line sensor 105, a time delay integration (TDI) sensor is suitable, for example.

Figure 2:
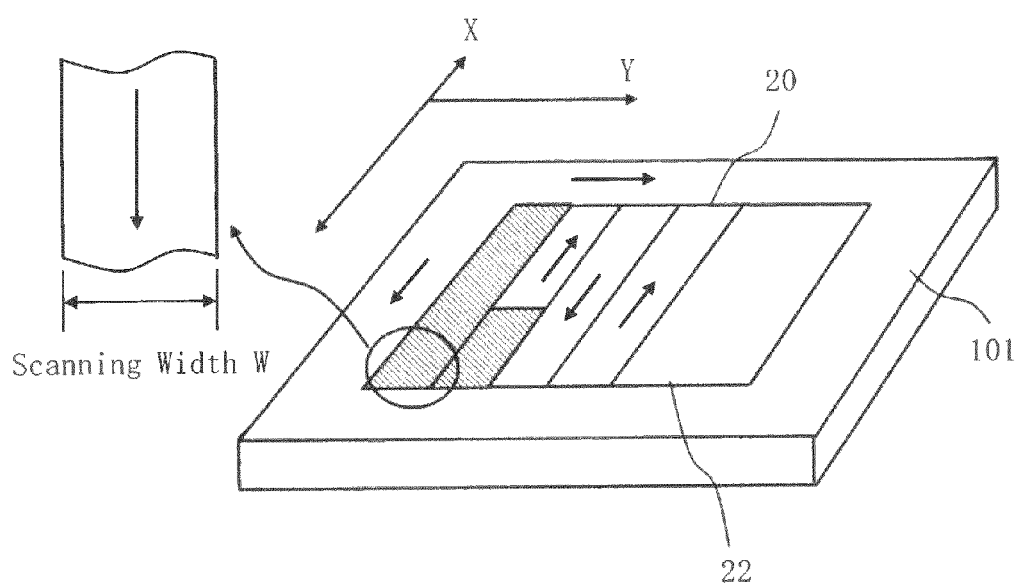
FIG. 2 is a schematic diagram describing a procedure for acquiring an optical image according to Embodiment 1.

FIG. 2 is a schematic diagram describing a procedure for acquiring an optical image according to Embodiment 1. An inspection region 22 is virtually divided into a plurality of strip-like inspection stripes 20, each having a scanning width W, in the Y direction, for example. The operation of the XYθ table 102 is controlled so that each divided inspection stripe 20 may be continuously scanned. By the movement of the XYθ table 102, optical images are acquired by the line sensor 105 which relatively moves in the X direction (first direction) continuously. That is, the line sensor 105 continuously captures optical images each having a scanning width W as shown in FIG. 2. It should be understood that the line sensor moves relatively to the movement of the XYθ table 102. According to Embodiment 1, after capturing an optical image in one inspection stripe 20, similarly, the line sensor 105 continuously captures another optical image having the scanning width W at a position shifted in the Y direction by a scanning width W, while moving in a direction reverse to the last image capturing direction. That is, the image capturing is repeated in the forward (FWD) and backward (BWD) direction, meaning going in a reverse direction when advancing and returning.

The pattern image focused on the line sensor 105 is photoelectrically converted by each light receiving element of the line sensor 105, and further analog-to-digital (A/D) converted by the sensor circuit 106. Pixel data of each inspection stripe 20 is stored in the stripe pattern memory 123. Then, the pixel data is sent to the correction circuit 140, with data indicating the position Y (italic character Y indicating a vector) of the photomask 101 on the XYθ table 102, output from the position circuit 107. The measurement data is 8-bit unsigned data, for example, and indicates a gray level (light quantity) of brightness of each pixel.

Figure 3:
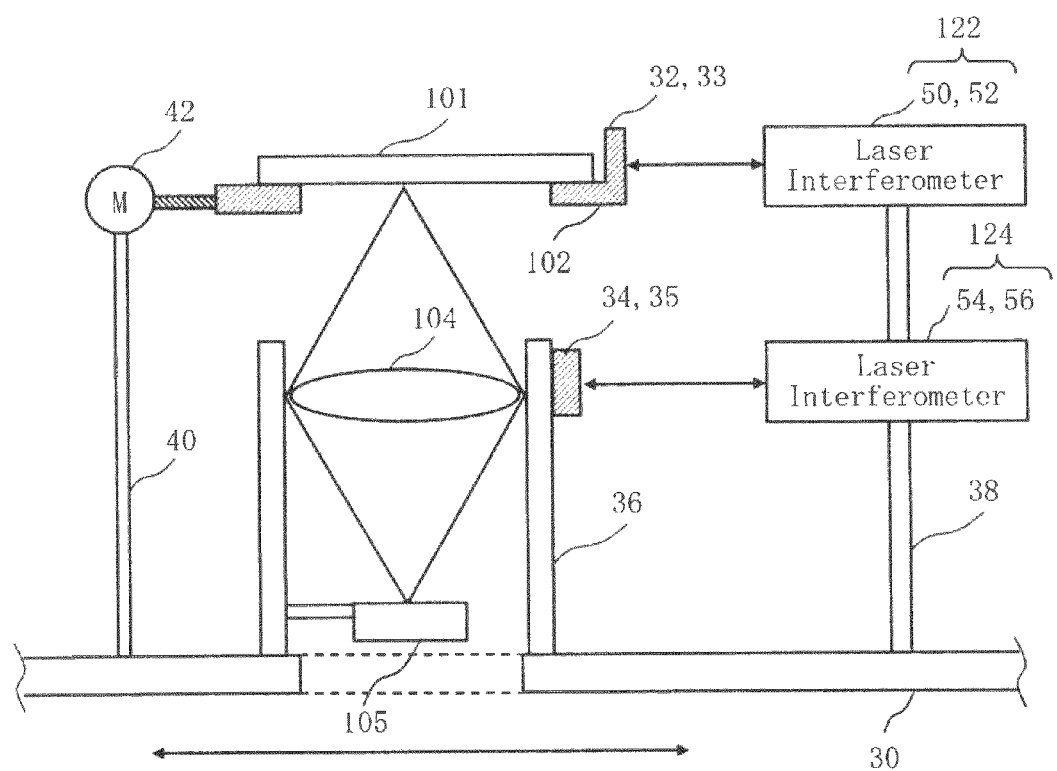
FIG. 3 shows an example of a state where a stage and a magnifying optical system are supported by a support member, according to Embodiment 1.

FIG. 3 shows an example of a state where the stage and the magnifying optical system are supported by a support member, according to Embodiment 1. On a pedestal 30, a support member 40 for fixing a motor 42 which operates the XYθ table 102 is arranged. Moreover, on the pedestal 30, there is arranged a support member 38 which supports the laser measuring system 122 (first laser measuring unit) for measuring the position of the XYθ table 102 and a laser measuring system 124 (second laser measuring unit) for measuring the position of the magnifying optical system 104. Furthermore, on the pedestal 30, there is arranged a support member 36, which supports the line sensor 105 with the magnifying optical system 104, at the optical center side between the support members 38 and 40. The motor 42 is a drive system such as a three-axis (X-Y-θ) motor for driving the photomask 101 in the X direction, the Y direction, and the θ direction as shown in FIG. 1. It should be understood that the motor 42 may be an independent motor for each of the three axes.

The position of the XYθ table 102 is measured with respect to the x direction and the y direction, respectively. Therefore, the laser measuring system 122 includes a laser interferometer 50 for measuring the position of the XYθ table 102 in the x direction, and a laser interferometer 52 for measuring the position of the XYθ table 102 in the y direction. Moreover, the XYθ table 102 includes a reflective mirror 32 which reflects a laser beam emitted from the laser interferometer 50, and a reflective mirror 33 which reflects a laser beam emitted from the laser interferometer 52. Data indicating the position X (the position X indicating a vector) of the XYθ table 102 measured by the laser measuring system 122 is sent to the position circuit 107.

The pedestal 30 expands and contracts by a thermal expansion or a deformation. Therefore, the relative position between the XYθ table 102 and the magnifying optical system 104 also changes with the expansion and contraction of the pedestal 30. If an image position is specified only by the position of the XYθ table 102, an error of the image position may arise in connection with a deviation of the magnifying optical system 104. Moreover, deformation or tilt of the support members 36 and 38 may be a factor of the error.

Then, according to Embodiment 1, the position of the magnifying optical system 104 is also measured in addition to the position of the XYθ table 102. The position of the magnifying optical system 104 is measured in the x direction and the y direction respectively, similarly to the XYθ table 102. Therefore, the laser measuring system 124 includes a laser interferometer 54 for measuring the position of the magnifying optical system 104 in the x direction, and a laser interferometer 56 for measuring the position of the magnifying optical system 104 in the y direction. Moreover, the support member 36 which supports the magnifying optical system 104 includes a reflective mirror 34 which reflects a laser beam emitted from the laser interferometer 54, and a reflective mirror 35 which reflects a laser beam emitted from the laser interferometer 56. Data indicating the position Z (the position Z indicating a vector) of the magnifying optical system 104 measured by the laser measuring system 124 is sent to the position circuit 107.

Figure 4:
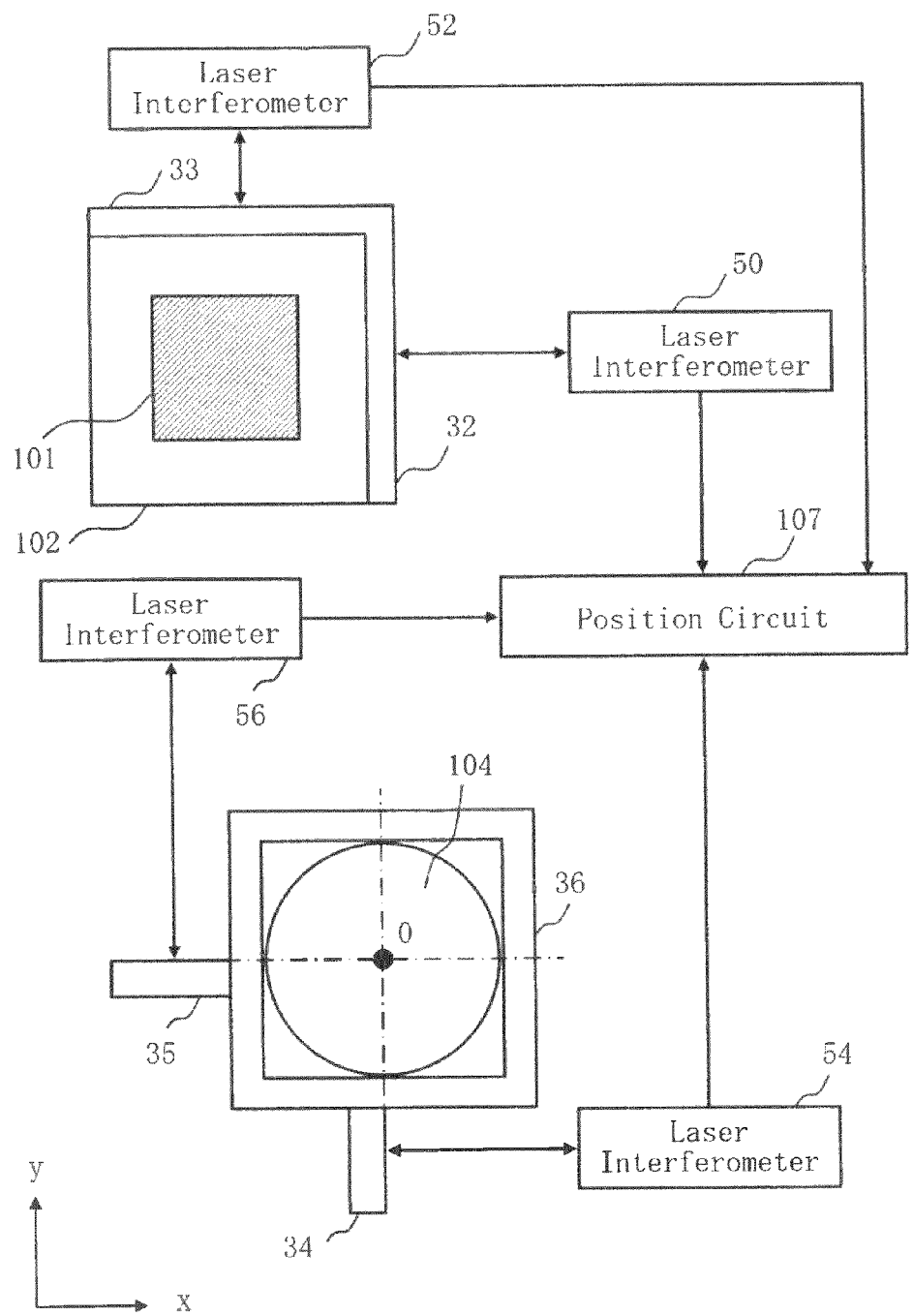
FIG. 4 is a plan view showing a state of measuring the position of the stage and the position of the magnifying optical system according to Embodiment 1.

FIG. 4 is a plan view showing the state of measuring the position of the stage and the position of the magnifying optical system according to Embodiment 1. In FIG. 4, there is arranged the reflective mirror 32 which has a reflective surface extending in the y direction, at the x-directional peripheral end of the XYθ table 102. Moreover, there is arranged the reflective mirror 33 which has a reflective surface extending in the x direction, at the y-directional peripheral end of the XYθ table 102. The reflective mirrors 32 and 33 may be united with the XYθ table 102, or combined after being formed as separate bodies. Alternatively, they may be assembled after being formed as separate bodies. The reflective mirror 32 reflects a laser beam emitted in the x direction from the laser interferometer 50. The reflective mirror 33 reflects a laser beam emitted in the y direction from the laser interferometer 52. Data indicating the position in each direction of the XYθ table 102, measured by the laser interferometers 50 and 52, is sent to the position circuit 107.

In FIG. 4, the magnifying optical system 104 is supported to be surrounded by the support member 36. The reflective mirror 34 is arranged at the position, in the −y direction (an example of the radial direction) from the optical center O of the magnifying optical system 104, on the periphery of the support member 36. The reflective mirror 34 has a reflective surface formed extending in the y direction from the optical center O of the magnifying optical system 104. It is preferable for the reflective surface of the reflective mirror 34 to be arranged at the position where the optical center O of the magnifying optical system 104 is in accordance with the coordinate in the y direction.

The reflective mirror 35 is arranged at the position, in the −x direction (an example of the radial direction) from the optical center O of the magnifying optical system 104, on the periphery of the support member 36. The reflective mirror 35 has a reflective surface formed extending in the x direction from the optical center O of the magnifying optical system 104. It is preferable for the reflective surface of the reflective mirror 35 to be arranged at the position where the optical center O of the magnifying optical system 104 is in accordance with the coordinate in the x direction.

The reflective mirror 34 reflects a laser beam emitted in the x direction from the laser interferometer 54. The reflective mirror 35 reflects a laser beam emitted in the y direction from the laser interferometer 56. Data indicating the position in each direction of the magnifying optical system 104, measured by the laser interferometers 54 and 56, is sent to the position circuit 107.

Figure 5:
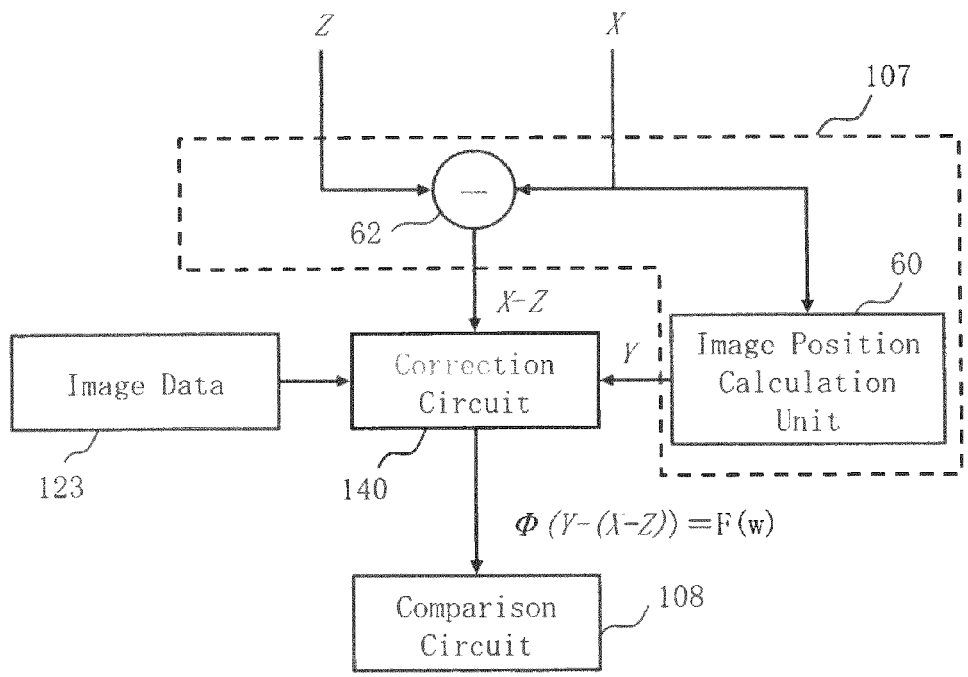
FIG. 5 shows the structure of a position circuit according to Embodiment 1.

FIG. 5 shows the structure of a position circuit according to Embodiment 1. In FIG. 5, an image position calculation unit 60 and a subtractor 62 are arranged in the position circuit 107. The image position calculation unit 60 calculates an image (pixel) position Y in the detected image, based on data indicating the position X of the XYθ table 102 measured by the laser measuring system 122, and outputs data indicating the image (pixel) position Y (position Y indicating a vector) to the correction circuit 140. The subtractor 62 calculate a difference (X−Z) (difference (X−Z) indicating a vector) between the position X of the XYθ table 102 measured by the laser measuring system 122 and the position Z of the magnifying optical system 104 measured by the laser measuring system 124, and outputs data indicating the difference (X−Z) which may change with the passage of time or a position, to the correction circuit 140 at all times or at an interval time. By using the laser interferometer, the position can be measured at nanometer (nm).

Figure 6:
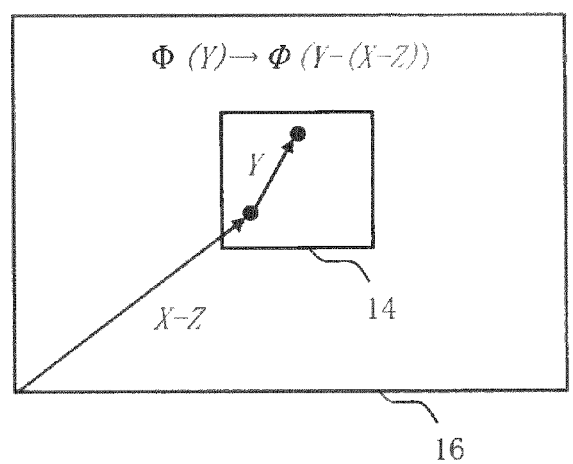
FIG. 6 is a schematic diagram for explaining an image correction according to Embodiment 1.

FIG. 6 is a schematic diagram for explaining an image correction according to Embodiment 1. In FIG. 6, a coordinate system 14 is a local coordinate system where the relative position between the XYθ table 102 and the magnifying optical system 104 is not considered. On the other hand, a coordinate system 16 is a global absolute coordinate system where the relative position between the XYθ table 102 and the magnifying optical system 104 is considered. When denoting pixel data of a captured image by Φ(Y) (Y indicating a vector) in the coordinate system 14, the pixel data of the captured image in the coordinate system 16 can be denoted by Φ(Y−(X−Z)) (Y−(X−Z) indicating a vector). Therefore, Φ(Y−(X−Z)) is the pixel data in the absolute coordinate system.

Then, the correction circuit 140 (correction unit) inputs each pixel data of an image from the stripe pattern memory 123, and corrects a captured pattern image by using the difference (X−Z) of the position X of the XYθ table 102 and the position Z of the magnifying optical system 104. When correcting, a difference (X−Z) at the time of each pixel data being received by the line sensor 105 is used as the difference (X−Z). It is preferable for a pattern image to be corrected per pixel. The pixel data Φ(Y−(X−Z)) in the absolute coordinate system after the correcting is output to the comparison circuit 108.

Figure 7A:
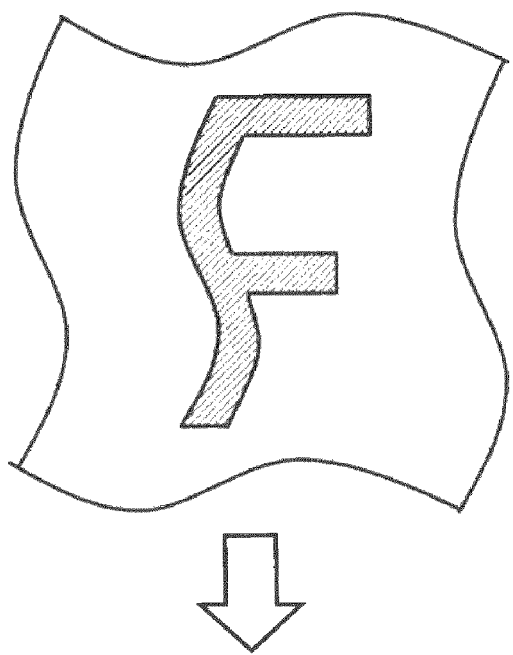
FIGS. 7A and 7B show an example of images before and after correcting according to Embodiment 1.
Figure 7B:
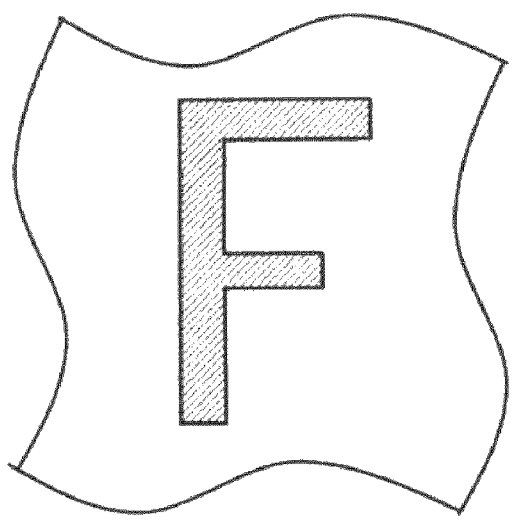

FIGS. 7A and 7B show an example of images before and after the correcting according to Embodiment 1. As shown in FIG. 7A, the image is distorted in the local coordinate system where the relative position between the XYθ table 102 and the magnifying optical system 104 is not considered. On the other hand, the distortion can be corrected by performing a correction at the relative position between the XYθ table 102 and the magnifying optical system 104 as shown in FIG. 7B. Particularly, by performing a correction per pixel, a highly precise distortion correction can be achieved as shown in FIG. 7B.

The die-to-database inspection is performed as follows: The comparison circuit 108 (inspection unit) inputs corrected pixel data from the correction circuit 140 for each inspection stripe 20. Then, an image of the size of the inspection stripe is cut into an inspection image of the size of 512×512 pixels, for example. The reference circuit 112 reads design data from the magnetic disk unit 109 through the control computer 110. The read design data of the photomask 101 is converted into image data of binary values or multiple values to generate reference data (reference image) whose size is the same as that of the image of measurement data. Then, the reference data is sent to the comparison circuit 108 (inspection unit).

Position alignment is performed between the measurement data and the reference data. Then, each pixel data of the measurement data and reference pixel data of the reference data are compared for each pixel according to a predetermined algorithm, and existence or nonexistence of a defect is judged based on the comparison result. Then, the comparison result is output, for example, to the magnetic disk drive 109, magnetic tape drive 115, FD 116, CRT 117, pattern monitor 118, or printer 119. Alternatively, it may be output to the outside. The inspection method is not limited to the die-to-database inspection, and it may be die-to-die inspection. The case of performing a die-to-die inspection will be described below.

Figure 8:
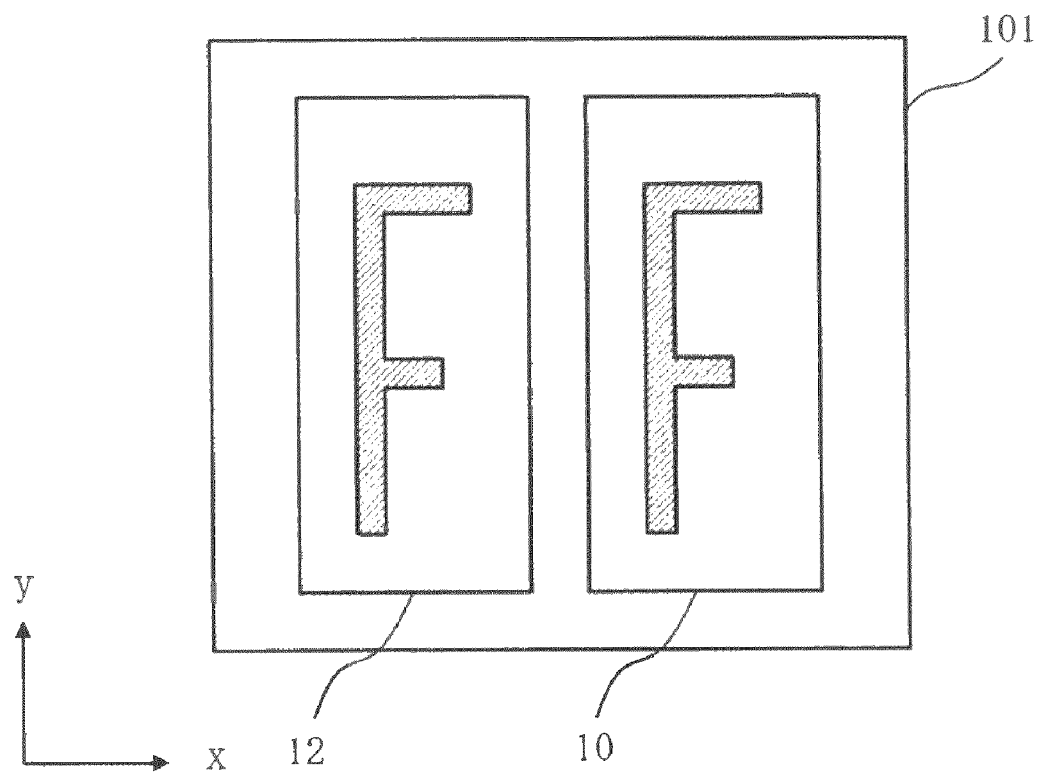
FIG. 8 shows an example of a photomask to be inspected by the die-to-die method according to Embodiment 1.

FIG. 8 shows an example of a photomask to be inspected by the die-to-die method according to Embodiment 1. In FIG. 8, the premise is that there are two or more inspection regions (die), written with the same design data, in the photomask 101. In FIG. 8, there are two inspection regions, an inspection region 10 and an inspection region 12 written based on the same design data, in the photomask 101. At this point, when performing the die-to-die inspection, as shown in FIG. 2, the entire inspection region including these two inspection regions 10 and 12 is virtually divided into a plurality of strip-like inspection stripes 20, each having a scanning width W, in the Y direction, for example. Therefore, the two corresponding regions are included in one inspection stripe 20. Then, the operation of the XYθ table 102 is controlled so that each divided inspection stripe 20 may be scanned continuously.

The die-to-die inspection is performed as follows: After measurement data of the inspection regions 10 and 12 imaged together is stored in the stripe pattern memory 123 for each inspection stripe 20, the position of each pixel data is corrected in the correction circuit 140. The corrected pixel data is sent to the comparison circuit 108 (inspection unit). Then, an image of the size of the inspection stripe is cut into an inspection image of the size of 512×512 pixels, for example. Position alignment of inspection images of corresponding regions of the inspection regions 10 and 12 is performed. Pixel data of each inspection image is compared with each other for each pixel according to a predetermined algorithm, to judge whether there is a defect of a pattern or not. The compared result is output, for example, to the magnetic disk drive 109, magnetic tape drive 115, FD 116, CRT 117, pattern monitor 118, or printer 119. Alternatively, it may be output to the outside.

As mentioned above, according to the present Embodiment, it is possible to accurately feedback the change of the relative position between the XYθ table 102 and the magnifying optical system 104 to the correction circuit 140. Then, by taking the change into consideration, it is possible to correct an image distortion caused by a positional deviation of the optical system. Therefore, a local positional deviation of a pattern can be detected. As a result, for example, a local positional deviation of a pattern can be detected in a mask for double exposure or double patterning. Moreover, as another consideration, it can be thought to make the pedestal 30 strong enough not to expand and contract. However, a tremendous cost is required for making the pedestal 30 strong. Furthermore, even if the pedestal 30 has been made strong, it is difficult to suppress the dimension change to be 1 nm or less. On the other hand, by using a laser interferometer, it is possible to measure a dimension of 1 nm or less, thereby performing image correction more simply and more accurately.

Embodiment 2

In Embodiment 1, a captured pattern image is corrected per pixel by using the difference (X−Z) between the position X of the XYθ table 102 and the position Z of the magnifying optical system 10. However, in Embodiment 2, correction is performed per subpixel smaller than a pixel.

Figure 9:
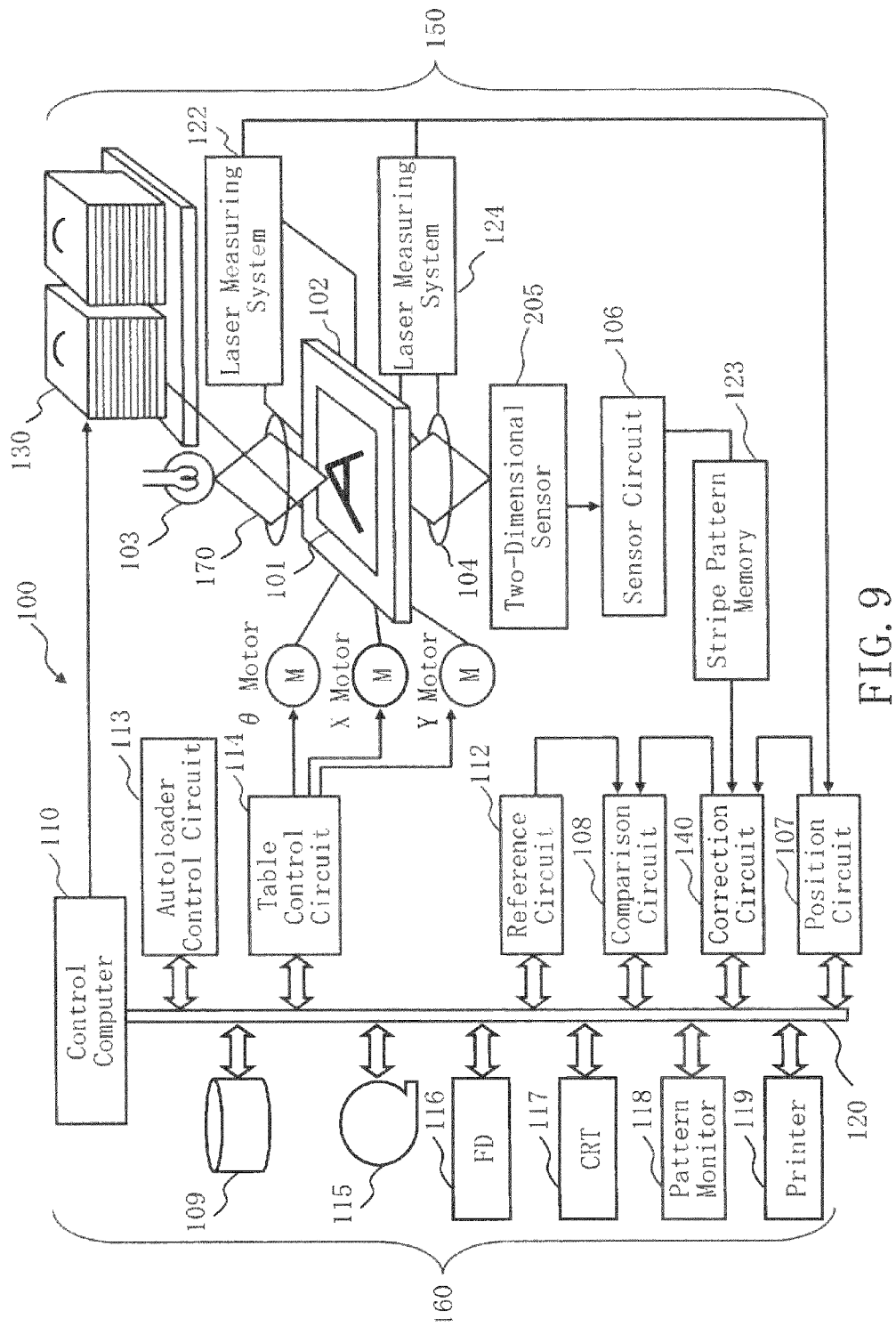
FIG. 9 is a schematic diagram showing a structure of a pattern inspection apparatus according to Embodiment 2.

FIG. 9 is a schematic diagram showing the structure of a pattern inspection apparatus according to Embodiment 2. FIG. 9 is the same as FIG. 1 except that a two-dimensional sensor 205 is provided instead of the line sensor 105.

Figure 10:
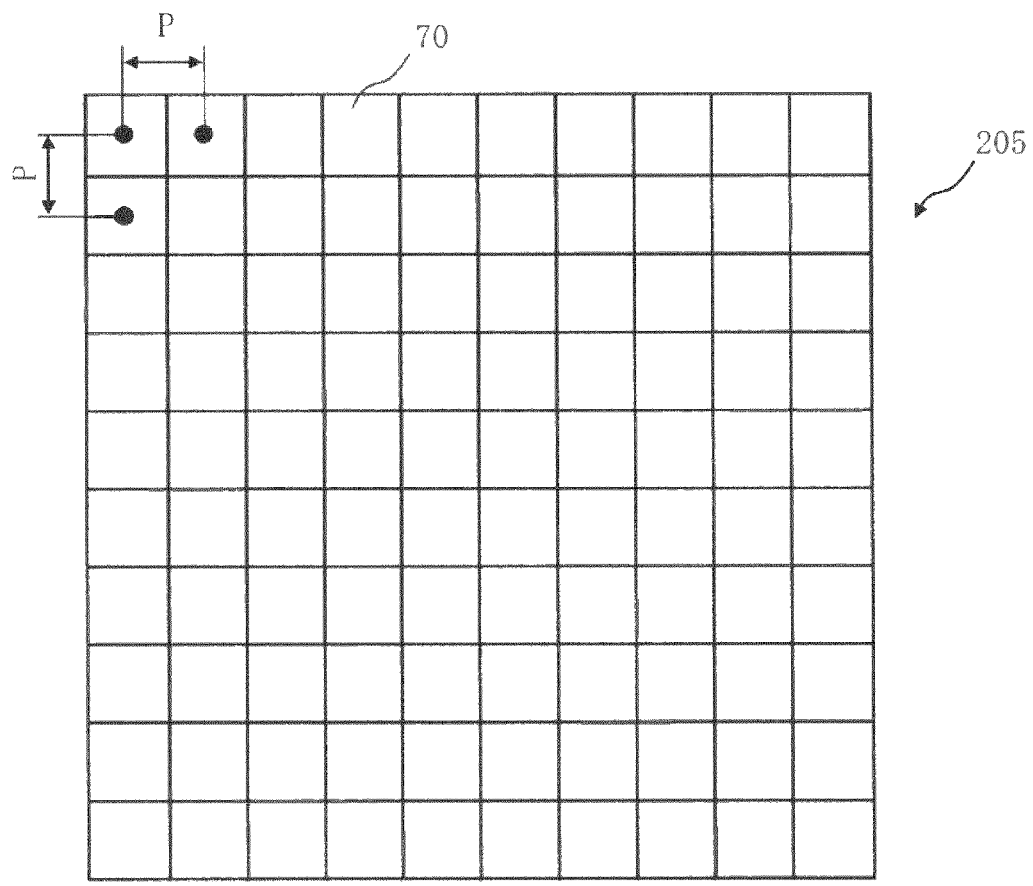
FIG. 10 is a schematic diagram showing an example of the array of light receiving elements of a two-dimensional sensor according to Embodiment 2.

FIG. 10 is a schematic diagram showing an example of the array of light receiving elements of a two-dimensional sensor according to Embodiment 2. In the two-dimensional sensor 205 of FIG. 10, a plurality of light receiving elements 70 are arranged in the x and y directions. The light receiving elements 70 are regularly arrayed at a pitch P in the x and y directions.

In this case, a plurality of light receiving elements 70 are arranged at a sampling interval L (also called a sampling frequency (spatial frequency)) obtained by the Nyquist condition expressed in the following formula, as the pitch P. The sampling interval L is defined by $L \leq \lambda/(4NA) \cdot M$ where NA indicates a maximum aperture angle at the photomask 101 side in the magnifying optical system 104, λ indicates a wavelength of illumination light from the light source 103, and M indicates a magnification of the magnifying optical system 104.

Figure 11:
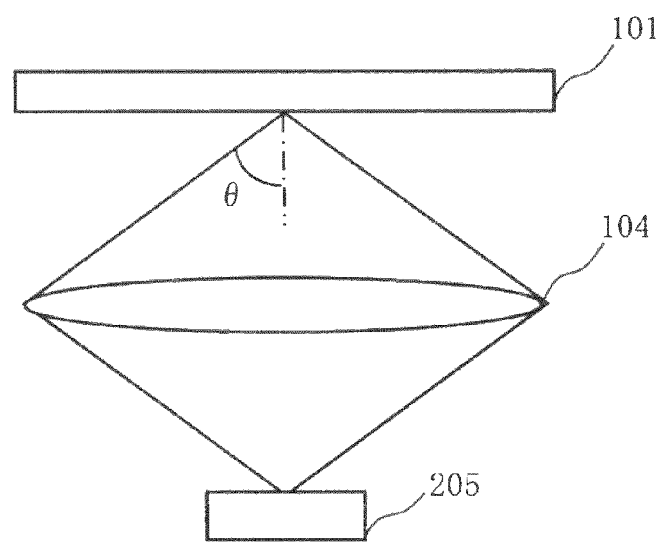
FIG. 11 is a schematic diagram for explaining the maximum aperture angle NA according to Embodiment 2.

FIG. 11 is a schematic diagram for explaining the maximum aperture angle NA according to Embodiment 2. In FIG.

11, the maximum aperture angle NA is expressed by NA=sin θ using an aperture angle θ against the optical axis at the photomask 101 side of the magnifying optical system 104.

In the case of using the two-dimensional sensor 205 as a TDI sensor, what is necessary is to set a movement speed V and a sampling time Δt so that V·Δt obtained by multiplying the movement speed V of the stage by the sampling time Δt of the output from the light receiving element 70 may be V·Δt=P=L≦λ/(4NA)·M.

Figure 12:
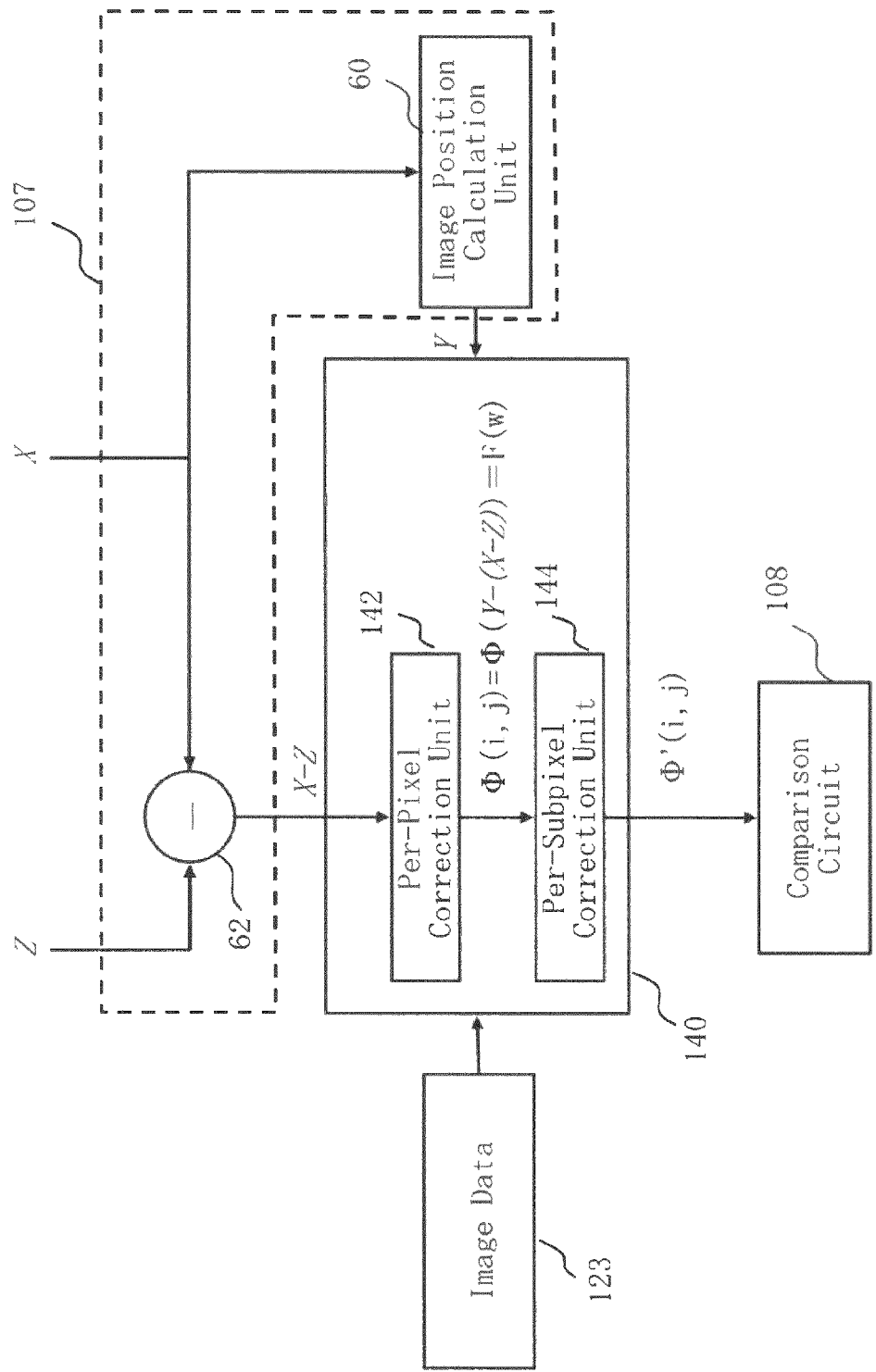
FIG. 12 is a schematic diagram showing the structure of a correction circuit according to Embodiment 2.

FIG. 12 is a schematic diagram showing the structure of a correction circuit according to Embodiment 2. In FIG. 12, a per-pixel correction unit 142 and a per-subpixel correction unit 144 which performs a correction per subpixel smaller than a pixel are arranged in the correction circuit 140. According to Embodiment 2, the per-pixel correction unit 142 (correction unit) in the correction circuit 140 inputs each pixel data of an image from the stripe pattern memory 123, and corrects a captured pattern image per pixel by using a difference (X–Z) between the position X of the XYθ table 102 and the position Z of the magnifying optical system 104. Embodiment 2 is similar to Embodiment 1 up to this point. Then, pixel data Φ(Y−(X−Z)) in the absolute coordinate system corrected by the per-pixel correction unit 142 is output to the per-subpixel correction unit 144. The pixel data Φ(Y−(X−Z)) corrected per pixel is then corrected by the per-subpixel correction unit 144.

At this point, an image intensity distribution acquired on the surface of the light receiving element 70 is defined to be I(x,y). In this image intensity distribution, distortion, etc. of the image has not been corrected for each subpixel. Then, there is required an image intensity distribution I'(x,y) which has been moved by an arbitrary distance including a subpixel, such as (ξ(x,y), η(x,y)), in order to correct a distortion of the coordinate system of the observation system. The image intensity distribution I'(x,y) is defined by I'(x,y)=I(x−ξ, y−η).

Next, image data obtained by sampling images at a fixed interval L is expressed in a two-dimensional scalar array. In the two-dimensional sensor 205, the light receiving elements 70 each having an aperture of a fixed area shall be regularly arranged at an even pitch in a two-dimensional grid-like array. Then, if the position of the light receiving element 70 constituting the two-dimensional sensor 205 is expressed as (i,j) by using indexes of the positions in the x and y directions, the relation between the image intensity distribution I and the pixel data Φ output from the two-dimensional sensor 205 at the pixel position (i,j) indicating the position of the light receiving element 70 can be expressed as Φ(i,j)=I(iL,jL). However, x=iL and y=jL.

Therefore, moved pixel data Φ'(i,j) can be expressed as Φ'(i,j)=I'(iL,jL)=I(iL−ξ,jL−η) where ξ=ξ(x,y) and η=η(x,y).

If utilizing the formula (interpolation formula) of Whittaker-Shannon at this point, the image intensity distribution I(x,y) can be expressed by the following equation (1):

$$I(x, y) = \sum_{n=-\infty}^{\infty} \sum_{m=-\infty}^{\infty} \Phi(n, m) \mathrm{sinc}\left(\frac{x - nL}{L}\right) \mathrm{sinc}\left(\frac{y - mL}{L}\right) \quad (1)$$

However, sin c(x)=sin(πx)/πx.

Therefore, the moved pixel data Φ'(i,j) can be expressed by the following equation (2):

$$\Phi'(i, j) = I'(iL, jL) \quad (2)$$

$$= I(iL - \xi, jL - \eta)$$

$$= \sum_{n=-\infty}^{\infty} \sum_{m=-\infty}^{\infty} \Phi(n, m) \mathrm{sinc}\left(\frac{iL - nL - \xi}{L}\right) \mathrm{sinc}\left(\frac{jL - mL - \eta}{L}\right)$$

By using the equation (2), the image intensity distribution I(x,y) being a continuous function can be restored from the measured pixel data Φ(i,j). Similarly, the corrected image intensity distribution I'(x,y) being a continuous function can be obtained from the image intensity distribution I'(x,y). Further, similarly, corrected pixel data Φ'(i,j) can be obtained by discretizing the corrected image intensity distribution I'(x,y) and performing a position correction of an arbitrary continuous quantity to the image.

Using the above relation, the per-subpixel correction unit 144 (correction unit) further corrects a captured pattern image per subpixel by using the formula of Whittaker-Shannon which uses the sampling interval L obtained by the Nyquist condition. That is, defining the pixel data Φ(Y−(X−Z)) in the absolute coordinate system corrected for each pixel by the per-pixel correction unit 142 as Φ(i,j), the per-subpixel correction unit 144 inputs Φ(i,j) and calculates pixel data Φ'(i,j) corrected per subpixel. Then, the pixel data Φ'(i,j) having been corrected per subpixel is output to the comparison circuit 108.

Figure 13:
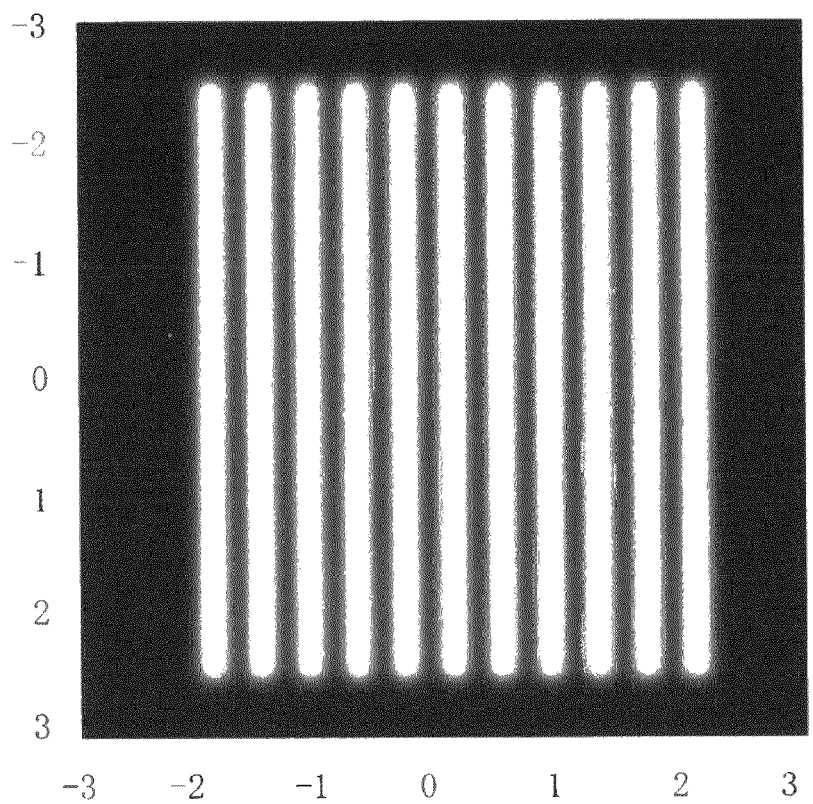
FIG. 13 shows an example of an image focused on the sensor surface of the inspection apparatus according to Embodiment 2.
Figure 14:
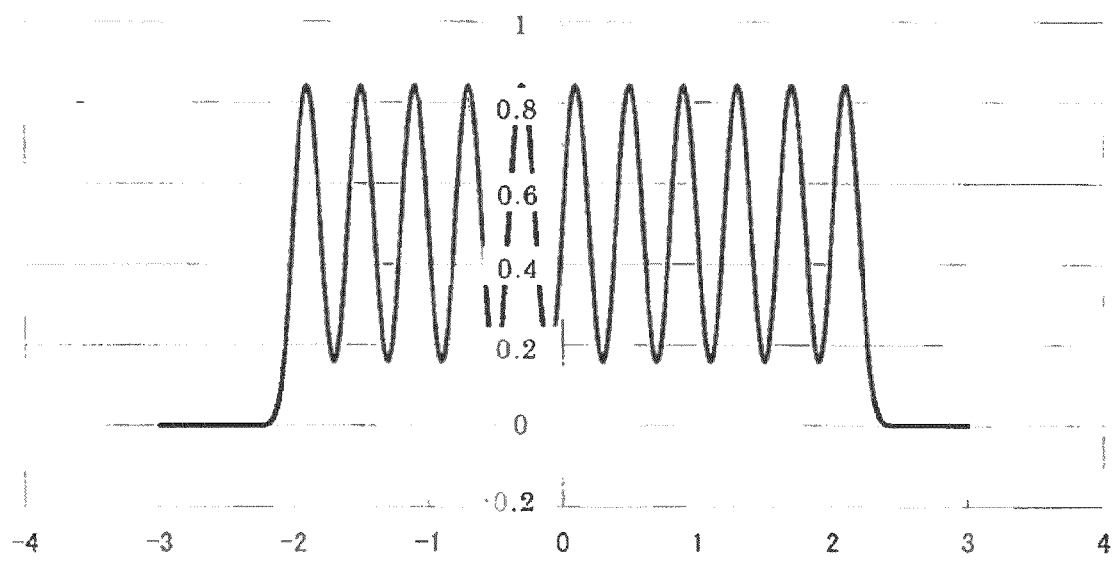
FIG. 14 is a graph of an ideal intensity distribution of an image with respect to the x-axis, showing for intelligibly indicating the state of the image intensity profile in FIG. 13.

FIG. 13 shows an example of an image focused on the sensor surface of the inspection apparatus according to Embodiment 2. For intelligibly indicating the state of the image intensity profile in FIG. 13, FIG. 14 shows a graph of an ideal intensity distribution of the image with respect to the x-axis. However, data actually output from the sensor circuit 196 does not show the ideal graph of FIG. 14.

Figure 15:
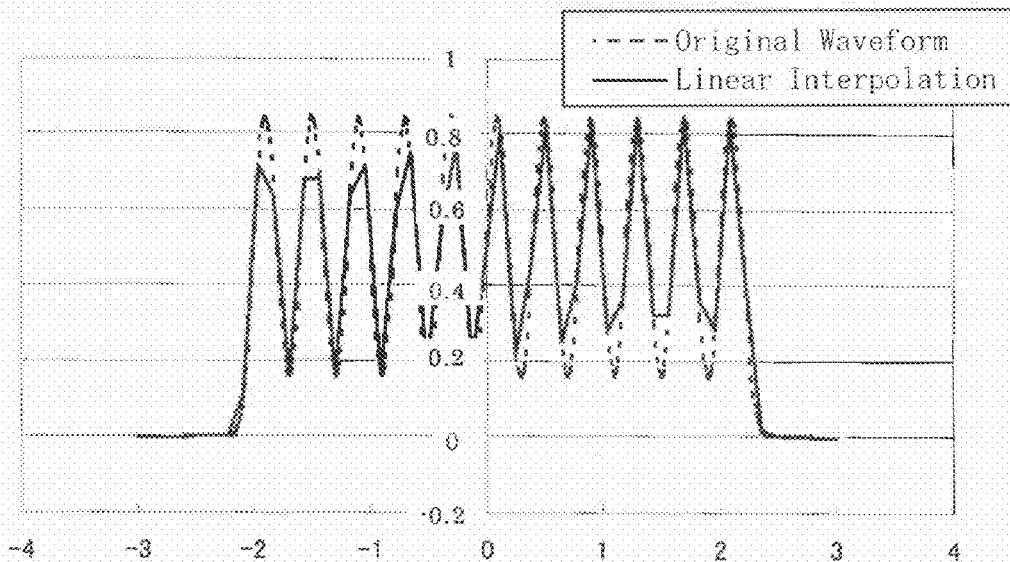
FIG. 15 is a graph showing an intensity distribution corresponding to FIG. 14 in the case of not performing a correction for each subpixel in Embodiment 2.

FIG. 15 is a graph showing an intensity distribution corresponding to FIG. 14 in the case of not performing a correction for each subpixel in Embodiment 2. When not performing a correction for each subpixel in Embodiment 2, data is imperfect as shown by the line graph of FIG. 15. The line graph is imperfect because the portions shown by the dotted lines in FIG. 15 are lack of the distribution. This is because the minimum pitch of the original image is close to the pitch of a detection pixel (light receiving element 70). Since linear interpolation of the profile between pixels has been performed for the portions different from the profile of the original image, the data is imperfect as shown by the line graph. When a pixel movement is performed by such interpolation, the error is large.

Figure 16:
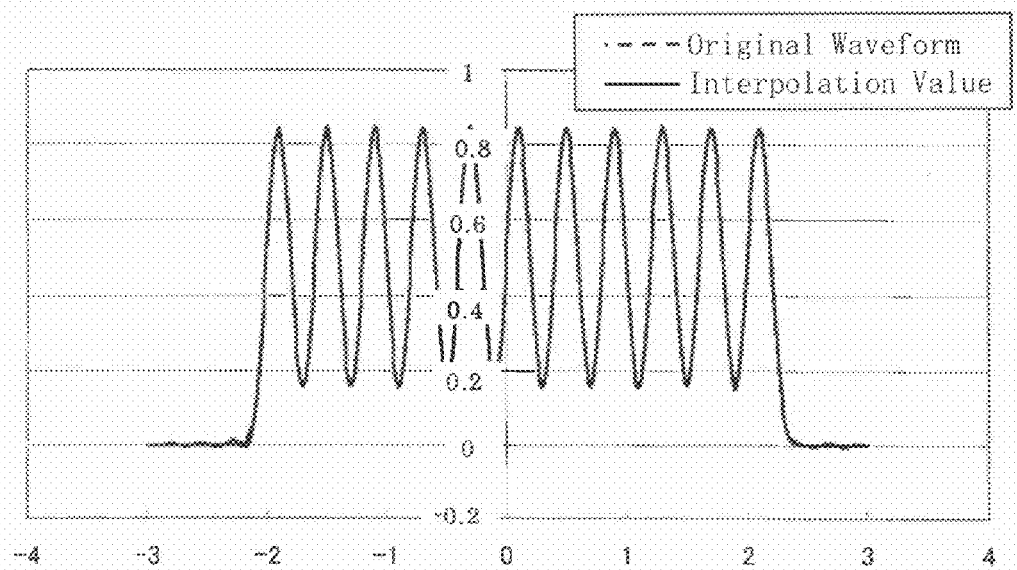
FIG. 16 is a graph showing an intensity distribution corresponding to FIG. 14 in the case of performing a correction for each subpixel in Embodiment 2.

FIG. 16 is a graph showing an intensity distribution corresponding to FIG. 14 in the case of performing a correction for each subpixel in Embodiment 2. If a captured pattern image is corrected per subpixel using the formula of Whittaker-Shannon that uses the sampling interval L obtained by the Nyquist condition, it becomes possible to be in accordance with the ideal intensity distribution as shown in FIG. 16, thereby greatly reducing errors. In addition, if the sampling interval L serving as a pixel pitch is defined as L≦λ/(4NA)·M−α that is stricter than the Nyquist condition, it is preferable because the computational amount can be reduced. Functions, such as Φ(i,j), Φ'(i,j), I(x,y), and I'(x,y) may be suitably transformed.

Although the two-dimensional sensor 205 is used in Embodiment 2, a one-dimensional line sensor may be used instead of the two-dimensional sensor 205 when performing a correction for each subpixel only in the direction (for example, y direction) orthogonal to the inspection direction (for example, x direction).

Figure 17:
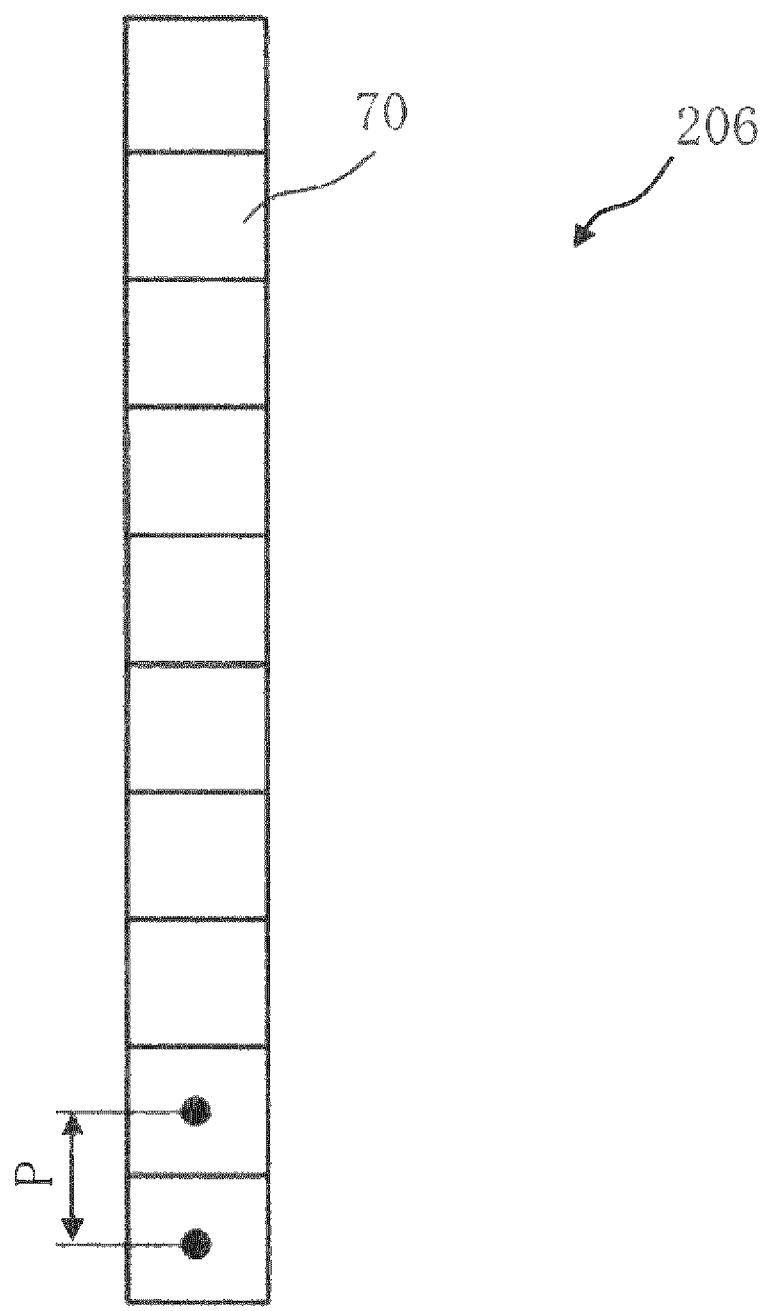
FIG. 17 is a schematic diagram showing an example of the array of the light receiving element of a one-dimensional line sensor according to Embodiment 2.

FIG. 17 is a schematic diagram showing an example of the array of the light receiving element of a one-dimensional line sensor according to Embodiment 2. In the one-dimensional line sensor 105 of FIG. 17, a plurality of light receiving elements 70 are arrayed in the y direction, for example. The light receiving elements 70 are regularly arrayed at a pitch P in the y direction. What is necessary is that a plurality of light receiving elements 70 are arranged regarding the sampling interval L defined by $L \leq \lambda/(4NA) \cdot M$ as the pitch P. This configuration makes it possible to perform a correction per subpixel in the y direction.

What is expressed by the term "unit" or "circuit" in the description above can be configured by computer programs. They may be implemented by software programs executed by the computer system. Alternatively, they may be executed by a combination of hardware and software, or a combination of hardware and firmware. When constituted by a program, the program is stored in a computer readable recording medium, such as the magnetic disk drive 109, magnetic tape drive 115, FD 116, or ROM (Read Only Memory). For example, each circuit, etc. in the autoloader control circuit 113, the table control circuit 114, the reference circuit 112, the comparison circuit 108, the correction circuit 140 and the position circuit 107 which constitute a calculation control unit may be configured by an electric circuit. Alternatively, they may be executed as software to be processed by the control computer 110, or executed by a combination of electric circuits and software.

While the embodiments have been described with reference to specific examples, the present invention is not limited thereto. For example, the inspection apparatus using a transmission optical system and a transmission light transmitted through the photomask 101 has been described in the above explanation, but the present invention is also effective to an inspection apparatus using a reflection optical system and a reflection light reflected from the photomask 101. In addition, the present invention includes applying an interpolation formula transformed a little by the rolloff method.

While description of the apparatus structure, control method, etc. not directly required for explaining the present invention is omitted, some or all of them may be suitably selected and used when needed. For example, although the structure of the control unit for controlling the inspection apparatus 100 is not described, it should be understood that a necessary control unit structure is to be selected and used appropriately.

In addition, any other pattern inspection apparatus and pattern inspection method that include elements of the present invention and that can be appropriately modified by those skilled in the art are included within the scope of the present invention.

Additional advantages and modification will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A pattern inspection apparatus comprising:
    a light source;
    a stage configured to mount thereon a substrate with a pattern formed thereon;
    a first laser measuring unit configured to measure a position of the stage by using a laser beam;
    a sensor configured to capture a pattern image obtained from the pattern, formed on the substrate, irradiated by light from the light source;
    an optical system configured to focus the light, which has penetrated the substrate on the stage, on the sensor;
    a second laser measuring unit configured to measure a position of the optical system, which focuses the light that has penetrated the substrate on the stage, by using a laser beam;
    a correction unit configured to correct a captured pattern image by using a difference between the position of the stage and the position of the optical system; and
    an inspection unit configured to inspect whether there is a defect of the pattern by using a corrected pattern image.

2. The apparatus according to claim 1 further comprising:
    a reflective mirror, having a reflective surface extending in a radial direction from an optical center of the optical system, configured to reflect the laser beam emitted by the second laser measuring unit, at the reflective surface.

3. The apparatus according to claim 1, wherein the correction unit corrects the pattern image per pixel.

4. The apparatus according to claim 1, wherein the correction unit corrects the captured pattern image per subpixel by using a formula of Whittaker-Shannon which uses a sampling interval obtained by Nyquist condition.

5. The apparatus according to claim 4, wherein the sampling interval L is obtained by an equation of $L \leq \lambda/(4NA) \cdot M$ using a maximum aperture angle NA at a side of the substrate in the optical system, a wavelength $\lambda$ of the light from the light source and a magnification M of the optical system.

6. The apparatus according to claim 4, wherein the correction unit further corrects the pattern image per subpixel after correcting the pattern image per pixel.

7. The apparatus according to claim 1, wherein the sensor includes a plurality of light receiving elements, which are arrayed at a pitch of a sampling interval obtained by Nyquist condition.

8. A pattern inspection method comprising:
    measuring, with a first laser measuring unit, a position of a stage configured to mount thereon a substrate with a pattern formed thereon, by using a laser beam;
    capturing a pattern image obtained from the pattern, formed on the substrate, irradiated by light from a light source, by using a sensor;
    measuring, with a second laser measuring unit, a position of an optical system which focuses the light, which has penetrated the substrate on the stage, on the sensor, by using a laser beam;
    correcting a captured pattern image by using a difference between the position of the stage and the position of the optical system; and
    inspecting whether there is a defect of the pattern by using a corrected pattern image.

9. The method according to claim 8, wherein the pattern image is corrected per pixel.

10. The method according to claim 8, wherein when correcting the pattern image, the pattern image is corrected per subpixel by using a formula of Whittaker-Shannon which uses a sampling period obtained by Nyquist condition.

* * * * *